United States Patent
Young et al.

[11] Patent Number: 5,891,019
[45] Date of Patent: Apr. 6, 1999

[54] TONGUE DEPRESSOR FOR CHILDREN AND METHOD

[76] Inventors: Rachel M. Young; Theodore P. Young, both of 500 SW. 168th Ter., Weston, Fla. 33326

[21] Appl. No.: 6,302

[22] Filed: Jan. 13, 1998

[51] Int. Cl.⁶ .................................................. A61B 11/02
[52] U.S. Cl. ........................................................... 600/240
[58] Field of Search ................... 600/240, 241, 600/242, 235, 237, 238, 239, 200

[56] References Cited

U.S. PATENT DOCUMENTS

| | | | |
|---|---|---|---|
| 2,425,946 | 8/1947 | Leach | 128/15 |
| 2,857,908 | 10/1958 | Cornfield | 600/240 |
| 3,324,849 | 6/1967 | Kravitz | 128/15 |
| 3,349,764 | 10/1967 | Edinger et al. | 128/16 |
| 3,867,927 | 2/1975 | Hergott | 600/240 X |
| 5,634,885 | 6/1997 | Kiro | 600/240 |

*Primary Examiner*—Beverly M. Flanagan
*Attorney, Agent, or Firm*—Oltman, Flynn & Kubler

[57] ABSTRACT

A tongue depressor includes a blade including a tongue contact portion, a flavor coating secured to the tongue contact portion, a stylized handle portion, and a structure for detaching the stylized handle portion from the tongue contact portion. The blade is preferably elongate and formed as a single piece of stiff and resilient material. The stylized handle portion includes an image, and preferably has a forward surface and the image is formed in the forward surface of the handle portion. The blade preferably has an edge with edge irregularities and the image extends to the blade edge so that the edge irregularities form part of the image. The image is alternatively printed on a sticker affixed to the handle portion. The image is still alternatively printed directly onto the handle portion. The image may be that of a person, and is optionally one of a variety of images constituting a collection. The flavor coating is preferably an edible food material. The structure for detaching may be a stress riser groove following a segmented path across the blade, forming a multifaceted edge upon blade breakage along the stress riser groove.

11 Claims, 9 Drawing Sheets

TONGUE DEPRESSOR FOR CHILDREN AND METHOD

BACKGROUND OF THE INVENTION

1. Field of the Invention:

The present invention relates generally to the field of medical and dental equipment. More specifically the present invention relates to a tongue depressor intended primarily for children, and having a flavor-coated tongue contact portion and a stylized handle portion which is detachable.

The construction of this tongue depressor makes oral examination enjoyable for children in at least two ways, so that they willingly cooperate with the examination. First the flavor-coating of the tongue contact portion makes placement of the depressor against the taste buds of the tongue pleasant so that children welcome its use, and the sweetness relaxes the pharyngeal muscles and thereby reduces the possibility of gagging. The tongue contact portion can also become a candy coated stick for consumption and continued enjoyment after the examination is completed. Second the stylized handle portion becomes an entertaining keepsake and toy, prolonging the enjoyed experience of the child so that he or she remembers it the next time an examination is needed. A method is provided including the step of breaking off the handle portion along a stress riser groove.

2. Description of the Prior Art:

There have long been various types of tongue depressors for bearing downwardly against the upper surface of a patient tongue to hold the tongue out of the way for viewing of the mouth and throat during oral examination. Modern tongue depressors are typically wooden or plastic slats, although other designs are known.

Kiro, U.S. Pat. No. 5,634,885, issued on Jun. 3, 1997, discloses a tongue depressor with a lollipop holder. Rather than placing a candy confection directly onto the tongue depressor, the stem of a lollipop is inserted into holder and fits into a longitudinal channel or slot in the depressor where it is removably secured in place. In another embodiment the holder is omitted and a slot or longitudinal bore is provided in the depressor for receiving a lollipop stem. A problem with Kiro is that molding or cutting a separate holder in addition to the depressor, or manufacturing a depressor with an axial bore for receiving a lollipop stem, makes the depressor relative costly to produce. Another problem is that the depressor is designed to become a toy for children, and the cost of the depressor may make giving it away impractical. Still another problem is that the medical examiner is forced to use whatever shape or size of lollipop candy portion is available to depress the tongue, since the lollipop candy portion appears to be the active portion of the depressor.

Edinger, et al., U.S. Pat. No. 3,349,764, issued on Oct. 31, 1967, teaches a self-illuminating tongue depressor with a detachable tongue blade. Edinger, et al., includes a hollow handle containing a rechargeable battery, a switch and a power circuit, and having a rod projecting forwardly therefrom with a light bulb mounted at the rod distal end. The light bulb is connected to the battery through the power circuit and is operated with the switch. An elongate and transparent plastic tongue contact portion having a longitudinal interior bore which removably receives the rod and bulb until the bulb is positioned within the remote end of the contact portion. The contact portion is then releasibly clipped to the handle portion. When examination is concluded, the contact portion is removed from the handle and discarded. A problem with Edinger, et al., is that it does not ease the concerns of children about placement of a foreign object into their mouths. Indeed, the mechanized appearance could make Edinger, et al. more intimidating than an ordinary tongue depressor. Another problem with Edinger, et al., is that it is complex and expensive to manufacture.

Leach, U.S. Pat. No. 2,425,945, issued on Aug. 19, 1947, reveals a confection-tongue depressor. Leach includes a wooden slat body member having a hole or a notch at its distal end into which a candy substance is secured, to make oral examination more pleasant for children. A problem with Leach is that no provision is made beyond the candy itself for making the depressor appealing to children.

Kravitz, U.S. Pat. No. 3,324,840, issued on Jun. 13, 1967, discloses a combination tongue depressor and swab. Kravitz includes a flat tongue blade and a cotton swab mounted at an end of an elongated swab rod. The swab rod is removably secured to a face of the tongue blade with two spaced apart brackets wrapping laterally around the tongue blade and rod, and can be slid longitudinally relative to the blade to cause the swab to protrude. The problems of Edinger, et al. are again presented.

It is thus an object of the present invention to provide a tongue depressor which makes oral examination a pleasant experience for children which they remember at the next examination so that they readily cooperate.

It is another object of the present invention to provide such a tongue depressor which is formed or molded as a single piece, with candy or other sweet substance affixed to the depressor member, and which has no need for provision of an internal chamber, so that unit cost is minimized.

It is still another object of the present invention to provide such a tongue depressor which is an elongate blade with a decorative handle portion and a candy-coated tongue contact portion, and which has a lateral stress riser between the handle portion and the tongue contact portion so that the decorative handle portion can be easily and cleanly broken away and retained by the child as a toy, and the used tongue contact portion discarded.

It is finally an object of the present invention to provide such a tongue depressor with a handle portion configured or marked in any of numerous and varied decorative configurations to be appealing to children as a collectible item.

SUMMARY OF THE INVENTION

The present invention accomplishes the above-stated objectives, as well as others, as may be determined by a fair reading and interpretation of the entire specification.

A tongue depressor is provided, including a blade including a tongue contact portion, a flavor coating secured to the tongue contact portion, a stylized handle portion, and a structure for detaching the stylized handle portion from the tongue contact portion.

The blade is preferably elongate and formed as a single piece of stiff and resilient material. The stylized handle portion includes an image, and preferably has a forward surface and the image is formed in the forward surface of the handle portion. The blade preferably has an edge with edge irregularities and the image extends to the blade edge so that the edge irregularities form part of the image. The image is alternatively printed on a sticker affixed to the handle portion. The image is still alternatively printed directly onto the handle portion. The image may be that of a person, and is optionally one of a variety of images constituting a collection. The flavor coating is preferably an edible food material.

The structure for detaching may be a stress riser groove following a segmented path across the blade, forming a multifaceted edge upon blade breakage along the stress riser groove. The structure for detaching is alternatively a stress riser groove following a linear path across the blade, forming a substantially rectilinear edge upon blade breakage along the stress riser groove. The structure for detaching still alternatively includes a stress riser groove following a curved path across the blade, forming a curved edge upon blade breakage along the stress riser groove.

The tongue depressor optionally additionally includes a recess in the tongue contact portion containing a quantity of candy forming the flavor coating. The depressor alternatively additionally includes a hole in the tongue contact portion, and a plug of candy fitted engagingly into the hole. The flavor coating still alternatively includes candy formed into a sleeve and removably fitted over the tongue contact portion.

A tongue depressor is further provided, including a blade including a blade edge, a tongue contact portion and a flavor coating affixed to the tongue contact portion, where the stylized handle portion includes an image extending to the blade edge and irregularities in the blade edge form part of the image.

A tongue depressor is provided, including a blade having a tongue contact portion and a stylized handle portion, and a candy sleeve removably fitted over the tongue contact portion. The depressor preferably additionally includes a structure for detaching the handle portion from the tongue contact portion.

A method is provided of using the above-described tongue depressor, including the steps of breaking the blade in two along the lateral stress riser element to separate the handle portion so that the handle portion becomes a toy.

BRIEF DESCRIPTION OF THE DRAWINGS

Various other objects, advantages, and features of the invention will become apparent to those skilled in the art from the following discussion taken in conjunction with the following drawings, in which.

DETAILED DESCRIPTION OF THE PREFERRED EMBODIMENTS

Figure 1:
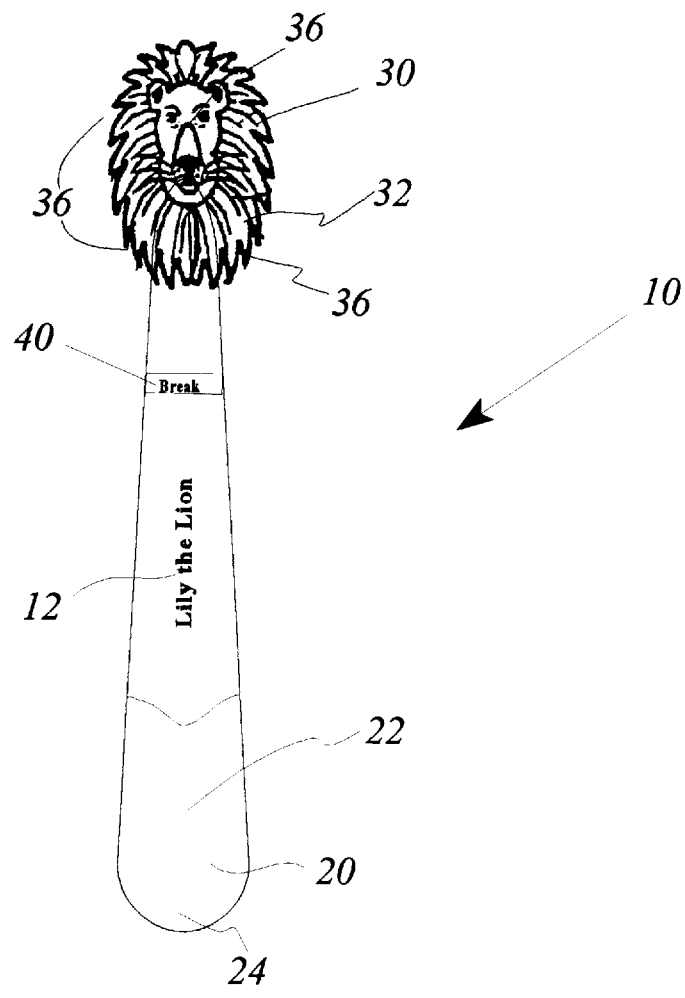
FIG. 1 is a front view of a preferred embodiment of the inventive tongue depressor, in this instance having a lion head with the contoured handle portion edge forming part of the lion head image. The stress riser groove is rectilinear. The flavor coating is shown extending entirely across the surface of the contact portion.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various FIGURES are designated by the same reference numerals.

First Preferred Embodiment

Referring to FIGS. 1–11, a tongue depressor 10 is disclosed having a tongue contact portion 20 with a flavor coating 22 and a stylized handle portion 30 separated by a stress-riser 40 so that handle portion 30 is detachable.

Depressor 10 preferably includes an elongate and singular blade 12 of stiff and resilient plastic, paper, wood or other material such as FDA approved polyethylene, polypropylene or polyvinyl chloride. Whatever material is used, blade 12 is preferably molded or otherwise formed as a single piece. The stylized pattern or image 32 on handle portion 30 is preferably a molded or cut in the blade 12 surface and extends out to the blade edges 36 so that blade 12 edge irregularities form part of the image 32. The image 32 can be three-dimensional, protruding forwardly, and possibly rearwardly, from or recessing into blade 12. See FIGS. 1, 2, 3 and 4. Alternatively, a painted paper or hologram sticker 34 portraying interesting imagery such as the head of an animal is glued to the handle portion 30, or the image 32 is printed directly on the blade 12 itself. The handle portion 30 image may be of a famous personality such as Babe Ruth, Silvester Stallone or Superman, and may be provided in a collectible series. See FIG. 7. Images 32 might be advertising tools for various products such as COCA COLA™ and COLGATE™, and become a promotional item. The flavor coating 22 is preferably any suitable edible food material such as chocolate, gun or sugar coated candies.

A key feature of the invention for most of the embodiments is the removability of the tongue contact portion 20 from the handle portion 30 by breaking the blade 12 in two along lateral stress riser groove or notch 40. This feature provides the option of separating the decorative handle portion 30 for retention by the child as a toy, while discarding the contaminated tongue contact portion 20. This option is particularly important where the child carries a contagious illness such as a cold or the flu. Alternatively the user may choose to clean and retain the blade 12 as a whole. The stress riser groove 40 preferably follows a segmented path across the blade 12, forming an attractive multifaceted edge upon breakage (See FIG. 2), but straight line and curved paths are also contemplated (See FIG. 7).

Figure 2:
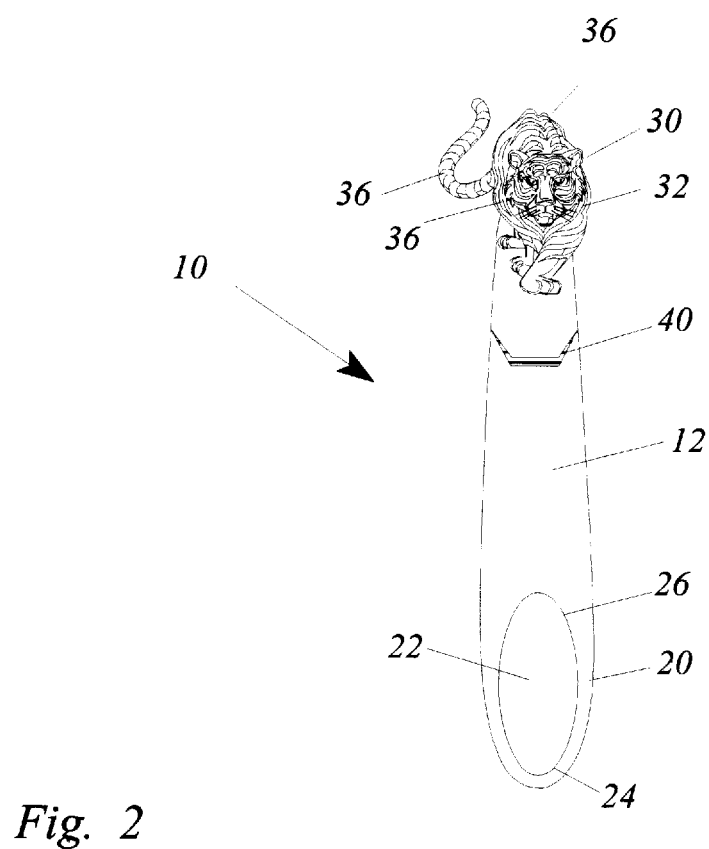
FIG. 2 is a view as in FIG. 1, in this instance having a complete tiger image formed in the handle portion. The stress riser groove is segmented. The flavor coating is shown fit into a recess in the contact portion.
Figure 3:
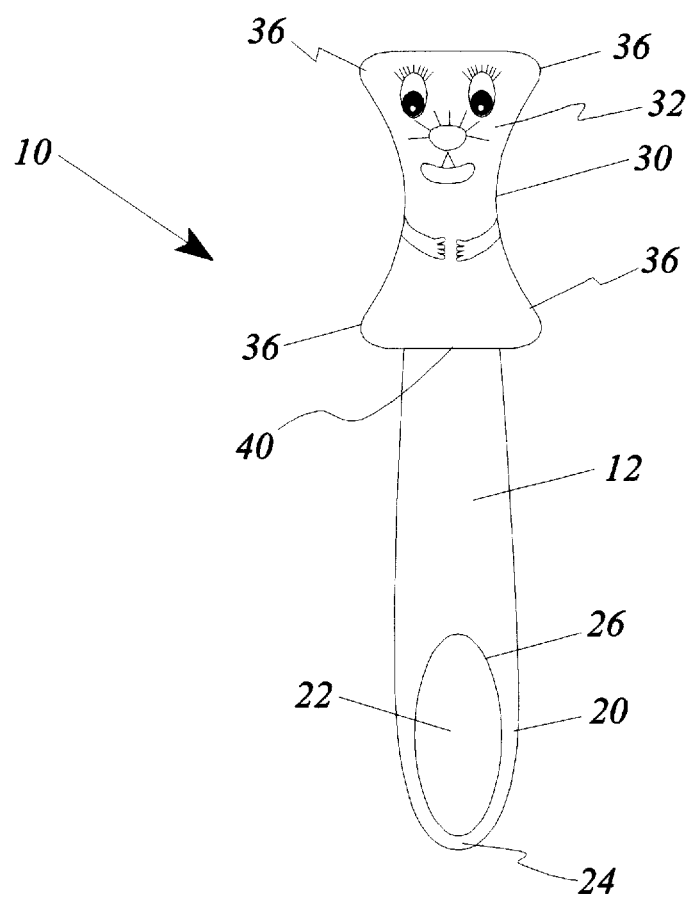
FIG. 3 is a view of the tongue depressor as in FIG. 2, having a cartoon character image.
Figure 4:
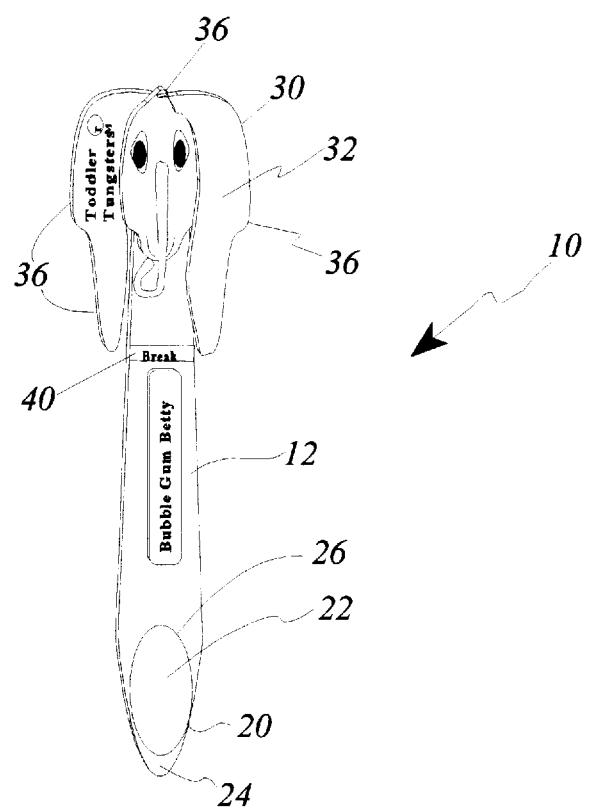
FIG. 4 is a view as in FIG. 3, having an elephant head image.
Figure 5:
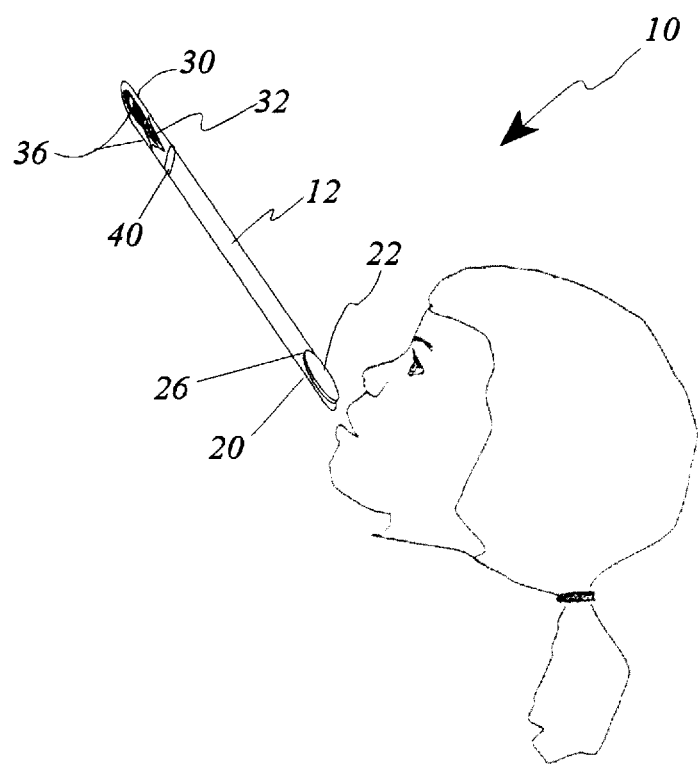
FIG. 5 is side view of a young girl about to receive the tongue contact portion in her mouth.
Figure 6:
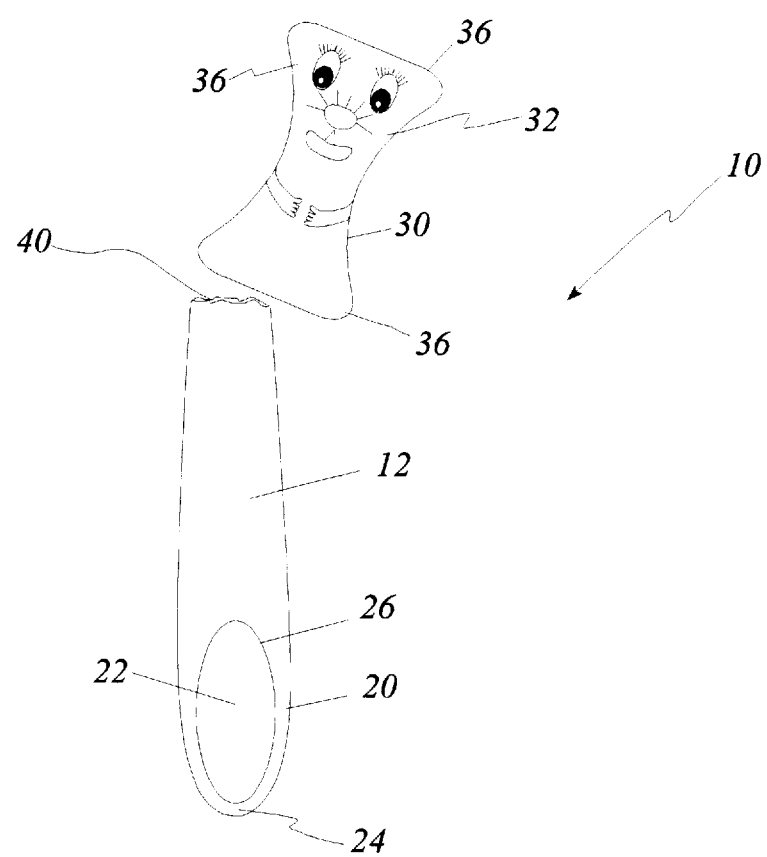
FIG. 6 is a view of the tongue depressor of FIG. 3, with the handle portion broken away from the tongue contact portion along the stress riser groove.
Figure 7:
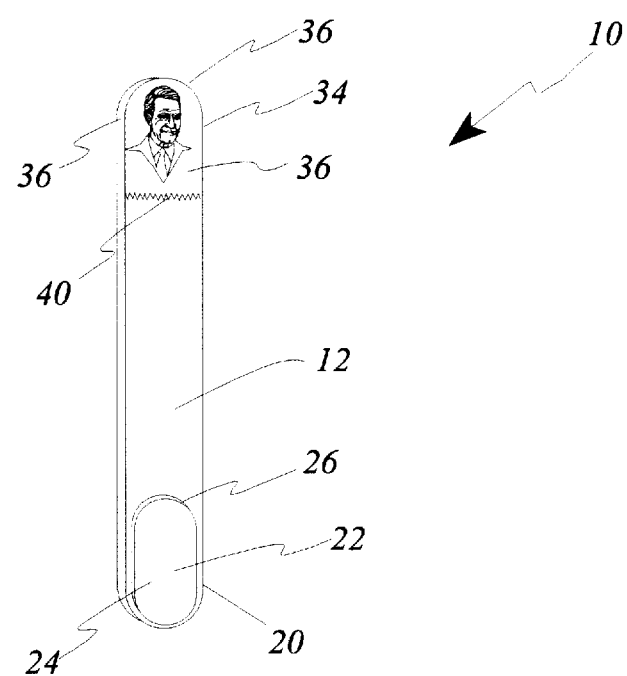
FIG. 7 is a view of a tongue depressor embodiment having an image in the form of a sticker printed with a picture of a person, and having a flavor coating extending laterally beyond the edges of the tongue contact portion.

Several embodiments of tongue depressor 10 are contemplated. For one version, the flavor coating 22 is affixed to the contact surface 24, or to both opposing surfaces, of the contact portion 20 by its own adhesive properties. See FIGS. 1, 6 and 7. For another version a recess 26 is made in the tongue contact portion 20 so that when the depressor 10 is immersed in a flowing bed of candy, the depression acts to trap a small amount of candy 22, thus forming a flavor coating 22 as shown in FIG. 2. For still another version, a hole 28 is provided in the tongue contact portion 20 and a plug 22a of candy is fitted engagingly into hole 28, such as by a combination of friction and natural adhesion, to form flavor coating 22. See FIGS. 10 and 11. Finally, the candy may be formed into a sleeve 22b and removably fitted over the contact portion 20 of blade 12. See FIG. 9.

Figure 8:
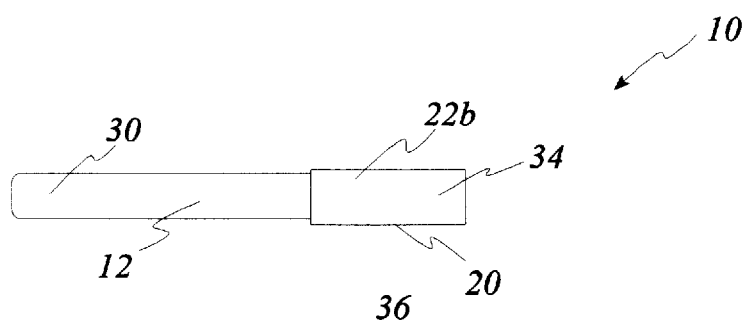
FIG. 8 is a view of a tongue depressor embodiment having no illustrated image and having a flavor coating in the form of a candy sleeve removably fitted onto the tongue contact portion.
Figure 9:
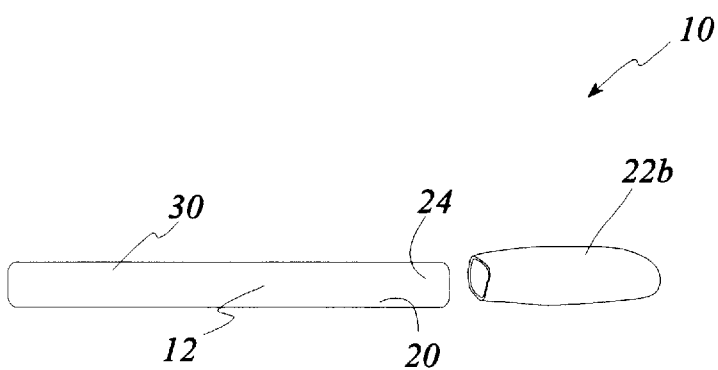
FIG. 9 is a view as FIG. 8 with the sleeve of candy removed.
Figure 10:
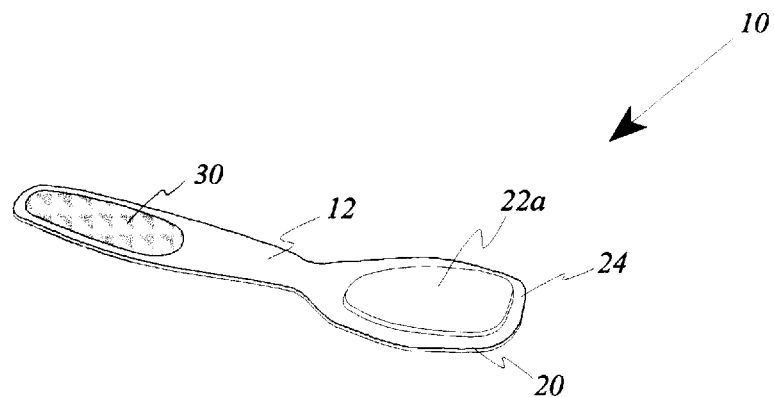
FIG. 10 is a perspective view of the stainless steel embodiment of the tongue depressor having a plug of candy fitted into a hole in the tongue contact portion.
Figure 11:
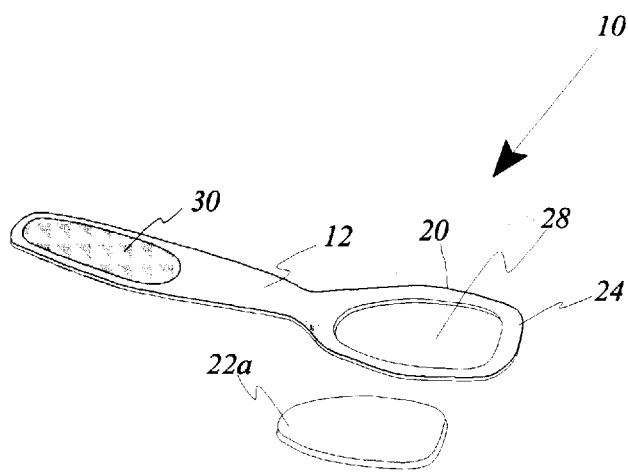
FIG. 11 is a view as in FIG. 10, with the plug of candy pulled out of the hole.

A reusable stainless steel blade 12 version having the candy sleeve 22b and no stress riser groove 40 is illustrated in FIGS. 8 and 9. The candy sleeve 22b is simply slid off the underlying stainless steel blade 12 upon completion of examination for consumption by the child. The candy filled hole 28 described above may be provided with the stainless steel blade 12. This version lacks the feature of a take-home toy portion.

Method

In practicing the invention, the following method may be used. The method includes the steps of breaking the blade 12 in two along stress riser groove 40 to separate the handle portion 30 from the tongue contact portion 20 so that the handle portion becomes a toy.

While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim as my invention:

1. A tongue depressor, comprising:
   a blade comprising a tongue contact portion having an opening therein, a stylized handle portion, and means for detaching said stylized handle portion from said tongue contact portion, wherein said means for detaching is a stress riser groove following a segmented path across said blade, forming a multifaceted edge upon blade breakage along said stress riser groove.

2. A tongue depressor according to claim 1, wherein said blade is elongate and formed as a single piece of stiff and resilient material.

3. A tongue depressor according to claim 1, wherein said stylized handle portion comprises an image.

4. A tongue depressor according to claim 3, wherein said handle portion has a forward surface and wherein said image is formed in said forward surface of said handle portion.

5. A tongue depressor according to claim 3, wherein said blade has an edge with edge irregularities and wherein said image extends to said blade edge such that said edge irregularities form part of said image.

6. A tongue depressor according to claim 3, wherein said image is printed on a sticker affixed to said handle portion.

7. A tongue depressor according to claim 3, wherein said image is printed directly onto said handle portion.

8. A tongue depressor according to claim 3, wherein said image is that of a person.

9. A tongue depressor according to claim 3, wherein said image is one of a variety of said images constituting a collection.

10. A tongue depressor, comprising:
    a blade comprising a tongue contact portion having an opening therein, a stylized handle portion, and means for detaching said stylized handle portion from said tongue contact portion, wherein said means for detaching is a stress riser groove following a linear path across said blade, forming a substantially rectilinear edge upon blade breakage along said stress riser groove.

11. A tongue depressor, comprising:
    a blade comprising a tongue contact portion having an opening therein, a stylized handle portion, and means for detaching said stylized handle portion from said tongue contact portion, wherein said means for detaching includes a stress riser groove following a curved path across said blade, forming a curved edge upon blade breakage along said stress riser groove.

* * * * *